US011446191B2

(12) United States Patent
Zerhusen et al.

(10) Patent No.: US 11,446,191 B2
(45) Date of Patent: Sep. 20, 2022

(54) PATIENT BED HAVING EXERCISE THERAPY APPARATUS

(71) Applicant: Hill-Rom Services, Inc., Batesville, IN (US)

(72) Inventors: Robert Mark Zerhusen, Cincinnati, OH (US); Lori Ann Zapfe, Milroy, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 148 days.

(21) Appl. No.: 16/822,091

(22) Filed: Mar. 18, 2020

(65) Prior Publication Data

US 2020/0330301 A1 Oct. 22, 2020

Related U.S. Application Data

(60) Provisional application No. 62/836,150, filed on Apr. 19, 2019.

(51) Int. Cl.

| | |
|---|---|
| ***A61G 7/015*** | (2006.01) |
| ***A63B 21/16*** | (2006.01) |
| ***A61G 7/018*** | (2006.01) |
| ***A63B 23/04*** | (2006.01) |

(Continued)

(52) U.S. Cl.

CPC ............. *A61G 7/015* (2013.01); *A61G 7/018* (2013.01); *A63B 21/1672* (2015.10); *A63B 22/0605* (2013.01); *A63B 23/0405* (2013.01); *A63B 24/0062* (2013.01); *A63B 2210/04* (2013.01); *A63B 2220/51* (2013.01)

(58) Field of Classification Search

CPC ............ A63B 22/0605; A63B 21/1672; A63B 21/068; A63B 21/00181; A63B 2210/04; A63B 2220/801; A63B 2220/803; A63B 23/0211; A63B 23/0405; A63B 24/0087; A63B 24/0062; A63B 2022/51; A63B 2022/0097; A63B 2022/0094; A61G 7/005; A61G 7/05; A61G 7/015; A61G 7/018; A61G 7/16; A61G 7/0514; A61G 7/0527; A61G 7/0524; A61G 13/02; A61G 13/06; A61G 13/08; A61H 1/0237; A61H 2201/0142; A61H 2201/1207; A61H 2201/1238; A61H 2201/1638; A61H 2201/1642; A61H 2201/5043; A61H 2201/5061

See application file for complete search history.

(56) References Cited

U.S. PATENT DOCUMENTS

| | | |
|---|---|---|
| 4,169,591 A | 10/1979 | Douglas |
| 4,557,480 A | 12/1985 | Dudley |
| 4,615,335 A | 10/1986 | Searcy |

(Continued)

FOREIGN PATENT DOCUMENTS

| | | |
|---|---|---|
| WO | 02076293 A1 | 10/2002 |
| WO | 2013134835 A1 | 9/2013 |
| WO | 2018081680 A1 | 5/2018 |

*Primary Examiner* — Nyca T Nguyen
*Assistant Examiner* — Zachary T Moore
(74) *Attorney, Agent, or Firm* — Barnes & Thornburg LLP

(57) ABSTRACT

A patient support apparatus may include a frame. A control module may be positioned on the frame. A graphical user interface may be in communication with the control module. An exercise apparatus may be coupled to the frame and may be in communication with the control module.

18 Claims, 12 Drawing Sheets

(51) Int. Cl.
*A63B 24/00* (2006.01)
*A63B 22/06* (2006.01)

(56) References Cited

U.S. PATENT DOCUMENTS

| | | | | |
|---|---|---|---|---|
| 4,635,931 | A | 1/1987 | Braennstam | |
| 4,925,184 | A * | 5/1990 | McJunkin, Jr. .... | A63B 22/0694 482/904 |
| 4,976,426 | A | 12/1990 | Szabo et al. | |
| 4,979,737 | A | 12/1990 | Kock | |
| 5,005,829 | A | 4/1991 | Caruso | |
| 5,207,628 | A | 5/1993 | Graham | |
| 5,312,315 | A | 5/1994 | Mortensen et al. | |
| 5,820,519 | A | 10/1998 | Slenker | |
| 5,984,844 | A | 11/1999 | Royer | |
| 6,053,850 | A | 4/2000 | Martinez et al. | |
| 6,152,855 | A | 11/2000 | Dean, Jr. et al. | |
| 6,695,795 | B2 | 2/2004 | Knoll | |
| 7,883,453 | B1 | 2/2011 | Cooper | |
| 7,996,080 | B1 | 8/2011 | Hartman et al. | |
| 8,249,714 | B1 | 8/2012 | Hartman et al. | |
| 8,923,978 | B1 | 12/2014 | Hartman et al. | |
| 8,950,026 | B2 * | 2/2015 | Valdemoros Tobia ........................ | A61B 5/447 5/613 |
| 9,038,218 | B1 * | 5/2015 | Heil ........................ | A61G 7/015 5/618 |
| 9,044,361 | B2 * | 6/2015 | Bell ........................ | G16H 40/63 |
| 9,492,341 | B2 * | 11/2016 | Huster ................... | G16H 10/60 |
| 9,586,077 | B2 | 3/2017 | Kabasso | |
| 9,603,768 | B1 | 3/2017 | Widmer et al. | |
| 9,687,401 | B2 * | 6/2017 | Alford ............... | A63B 23/0417 |
| 2003/0135129 | A1 | 7/2003 | Cusimano et al. | |
| 2003/0207734 | A1 | 11/2003 | La Stayo et al. | |
| 2004/0082438 | A1 | 4/2004 | LaStayo et al. | |
| 2004/0092372 | A1 | 5/2004 | Clark, III | |
| 2004/0157708 | A1 | 8/2004 | Matthews | |
| 2005/0251067 | A1 | 11/2005 | Terry | |
| 2006/0199700 | A1 | 9/2006 | LaStayo et al. | |
| 2011/0040215 | A1 | 2/2011 | Knoll | |
| 2011/0237407 | A1 | 9/2011 | Kaleal et al. | |
| 2014/0009917 | A1 * | 1/2014 | Westermann .......... | A61G 7/002 5/616 |
| 2016/0016036 | A1 | 1/2016 | Barriskill et al. | |
| 2016/0045383 | A1 | 2/2016 | Soo | |
| 2018/0092801 | A1 | 4/2018 | Shockley, Jr. et al. | |

* cited by examiner

PATIENT BED HAVING EXERCISE THERAPY APPARATUS

CROSS-REFERENCE TO RELATED APPLICATIONS

This application claims priority under 35 U.S.C. § 119(e) to U.S. Provisional Patent Application Ser. No. 62/836,150, filed Apr. 19, 2019, which is expressly incorporated by reference herein.

BACKGROUND

The disclosed embodiments are related to a patient support apparatus, and more particularly, to a patient support apparatus having physical therapy components.

Early mobility is a common theme for physical therapy applied to acute patients in an effort to accelerate their recovery in the Intensive Care Unit (ICU). Synonymous with early mobility is the quads or squat therapy, which involves the patient doing what is akin to deep knee bends. There are some devices that can accomplish quads or squat therapy, however none of these devices are integrated into an ICU bed and none of the devices reach beyond a simple quads type therapy. It is desired to incorporate physical therapy devices that engage more than just the quads, for example, the 3 basic muscle groups, quads, arms, and the core. By incorporating additional therapy capabilities, early mobility can be extended to patients that may have a disability preventing them from using a quad based physical therapy. In addition, by engaging additional muscle groups a patient's recovery may be accelerated.

SUMMARY

The present disclosure includes one or more of the features recited in the appended claims and/or the following features which, alone or in any combination, may comprise patentable subject matter.

According to an aspect of the disclosed embodiments, a patient support apparatus may include a frame. A headboard and footboard may be coupled to the frame. A pair of side rails may be coupled to the frame. A control module may be positioned on the frame. A graphical user interface may be in communication with the control module. An exercise apparatus may be coupled to the frame and may be in communication with the control module. The control module may be configured to control an operation of the exercise apparatus. The graphical user interface may display information related to the operation of the exercise apparatus.

In some embodiments, the graphical user interface may include user inputs that enable a user to input an exercise regimen into the control module. The control module may control the exercise apparatus based on the exercise regimen. The control module may track the user's progress of the exercise regimen. The graphical user interface may display data related to the user's progress of the exercise regimen. The exercise regimen may include at least one of a number of sets, a number of repetitions, and a resistance.

Optionally, the graphical user interface may be positioned on the footboard. A motion switch may track the motion of the exercise apparatus. The motion switch may transmit data related to the motion of the exercise apparatus to the control module. The exercise apparatus may include a resistance control to control a resistance of the exercise apparatus. The resistance control may include a motor. The resistance control may include a resistance band. The resistance control may be controlled with user inputs on the graphical user interface.

It may be desired that the exercise apparatus includes foot pedals coupled to the footboard. The frame may include a foot section that lowers to enable use of the foot pedals.

It may be contemplated that the exercise apparatus includes a head section of the frame. The head section may raise and lower as a user performs sit ups. The head section may include a strain gauge to measure movement of the user relative to the head section. A motor may raise and lower the head section.

In some embodiments, the exercise apparatus may include a pair of arm levers. Each arm lever of the pair of arm levers may be coupled to the frame.

According to another aspect of the disclosed embodiments, a patient support apparatus may include a frame. A headboard and footboard may be coupled to the frame. A pair of side rails may be coupled to the frame. A control module may be positioned on the frame. A graphical user interface may be communication with the control module. The graphical user interface may enable a user to input an exercise regimen into the control module. An exercise apparatus may be coupled to the frame and may be in communication with the control module. The control module may be configured to control an operation of the exercise apparatus. The control module may control the exercise apparatus based on the exercise regimen. The exercise apparatus may include a resistance control to control a resistance of the exercise apparatus based on the exercise regimen.

In some embodiments, the graphical user interface may be positioned on the footboard. The graphical user interface may be positioned on one of the pair of side rails.

Optionally, the control module may track the user's progress of the exercise regimen. The graphical user interface may display data related to the user's progress of the exercise regimen. The exercise regimen may include at least one of a number of sets, a number of repetitions, and a resistance.

It may be contemplated that a motion switch tracks the motion of the exercise apparatus. The motion switch may transmit data related to the motion of the exercise apparatus to the control module. The exercise apparatus may include a resistance control to control a resistance of the exercise apparatus. The resistance control may include a motor. The resistance control may include a resistance band. The resistance control may be controlled with user inputs on the graphical user interface.

It may be desired that the exercise apparatus includes foot pedals coupled to the footboard. The frame may include a foot section that lowers to enable use of the foot pedals.

Optionally, the exercise apparatus may include a head section of the frame. The head section may raise and lower as a user performs sit ups. The head section may include a strain gauge to measure movement of the user relative to the head section. A motor may raise and lower the head section.

It may be contemplate that the exercise apparatus includes a pair of arm levers. Each arm lever of the pair of arm levers may be coupled to the frame.

According to yet another aspect of the disclosed embodiments, a patient support apparatus may include a frame. A headboard and footboard may be coupled to the frame. A pair of side rails may be coupled to the frame. A control module may be positioned on the frame. A graphical user interface may be in communication with the control module. The graphical user interface may include user inputs that enable a user to input an exercise regimen into the control module. The exercise regimen may include at least one of a number of sets, a number of repetitions, and a resistance. An exercise apparatus may be coupled to the frame and may be in communication with the control module. The control module may be configured to control an operation of the exercise apparatus based on the exercise regimen. The control module may track the user's progress of the exercise regimen. The graphical user interface may display data related to the user's progress of the exercise regimen.

It may be desired that the graphical user interface is positioned on the footboard. The graphical user interface may positioned on one of the pair of side rails.

In some embodiments, a motion switch may track the motion of the exercise apparatus. The motion switch may transmit data related to the motion of the exercise apparatus to the control module. The exercise apparatus may include a resistance control to control a resistance of the exercise apparatus. The resistance control may include a motor. The resistance control may include a resistance band. The resistance control may be controlled with user inputs on the graphical user interface.

In some embodiments, the exercise apparatus may include foot pedals coupled to the footboard. The frame may include a foot section that lowers to enable use of the foot pedals.

Optionally, the exercise apparatus may include a head section of the frame. The head section may raise and lower as a user performs sit ups. The head section may include a strain gauge to measure movement of the user relative to the head section. A motor may raise and lower the head section.

It may be contemplated that the exercise apparatus includes a pair of arm levers. Each arm lever of the pair of arm levers may be coupled to the frame.

According to a further aspect of the disclosed embodiments, a patient support apparatus may include a frame. A headboard and footboard may be coupled to the frame. A pair of side rails may be coupled to the frame. A control module may be positioned on the frame. A graphical user interface may positioned on at least one of the footboard and one of the pair of side rails and may be in communication with the control module. Foot pedals may be coupled to the foot board and may be in communication with the control module. The control module may be configured to control an operation of the foot pedals. The graphical user interface may display information related to the operation of the foot pedals.

Optionally, the frame may include a foot section that may lower to enable use of the foot pedals. The graphical user interface may include user inputs that may enable a user to input an exercise regimen into the control module. The control module may control the foot pedals based on the exercise regimen. The control module may track the user's progress of the exercise regimen. The graphical user interface may display data related to the user's progress of the exercise regimen. The exercise regimen may include at least one of a number of sets, a number of repetitions, and a resistance.

It may be contemplated that a motion switch tracks the motion of the foot pedals. The motion switch may transmit data related to the motion of the foot pedals to the control module. The foot pedals may include a resistance control to control a resistance of the foot pedals. The resistance control may include a motor. The resistance control may include a resistance band. The resistance control may be controlled with user inputs on the graphical user interface.

According to yet a further aspect of the disclosed embodiments, a patient support apparatus may include a frame. A headboard and footboard may be coupled to the frame. A pair of side rails may be coupled to the frame. A control module may be positioned on the frame. A graphical user interface may be coupled to at least one of the footboard and one of the pair of side rails and may be in communication with the control module. An exercise apparatus may be coupled to the frame and may be in communication with the control module. The exercise apparatus may include a head section of the frame that may raise and lower as a user performs sit ups. The control module maybe configured to control an operation of the exercise apparatus. The graphical user interface may display information related to the operation of the exercise apparatus.

In some embodiments, the head section may include a strain gauge to measure movement of the user relative to the head section. A motor may raise and lower the head section.

Optionally, the graphical user interface may include user inputs that enable a user to input an exercise regimen into the control module. The control module may control the exercise apparatus based on the exercise regimen. The control module may track the user's progress of the exercise regimen. The graphical user interface may display data related to the user's progress of the exercise regimen. The exercise regimen may include at least one of a number of sets, a number of repetitions, and a resistance.

It may be contemplated that a motion switch tracks the motion of the exercise apparatus. The motion switch may transmit data related to the motion of the exercise apparatus to the control module. The exercise apparatus may include a resistance control to control a resistance of the exercise apparatus. The resistance control may include a motor. The resistance control may include a resistance band. The resistance control may be controlled with user inputs on the graphical user interface.

According to an additional aspect of the disclosed embodiments, a patient support apparatus may include a frame. A headboard and footboard may be coupled to the frame. A pair of side rails may be coupled to the frame. A control module may be positioned on the frame. A graphical user interface may be coupled to at least one of the footboard and one of the pair of side rails and may be in communication with the control module. A pair of arm levers may be in communication with the control module. Each arm lever of the pair of arm levers may be coupled to the frame. The control module may be configured to control an operation of the exercise apparatus. The graphical user interface may display information related to the operation of the exercise apparatus.

It may be desired that the graphical user interface includes user inputs that enable a user to input an exercise regimen into the control module. The control module may control the exercise apparatus based on the exercise regimen. The control module may track the user's progress of the exercise regimen. The graphical user interface may display data related to the user's progress of the exercise regimen. The exercise regimen may include at least one of a number of sets, a number of repetitions, and a resistance.

Optionally, a motion switch may track the motion of the exercise apparatus. The motion switch may transmit data related to the motion of the exercise apparatus to the control module. The exercise apparatus may include a resistance control to control a resistance of the exercise apparatus. The resistance control may include a motor. The resistance control may include a resistance band. The resistance control may be controlled with user inputs on the graphical user interface.

Additional features, which alone or in combination with any other feature(s), such as those listed above and/or those listed in the claims, can comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures in which.

DETAILED DESCRIPTION

Figure 1:
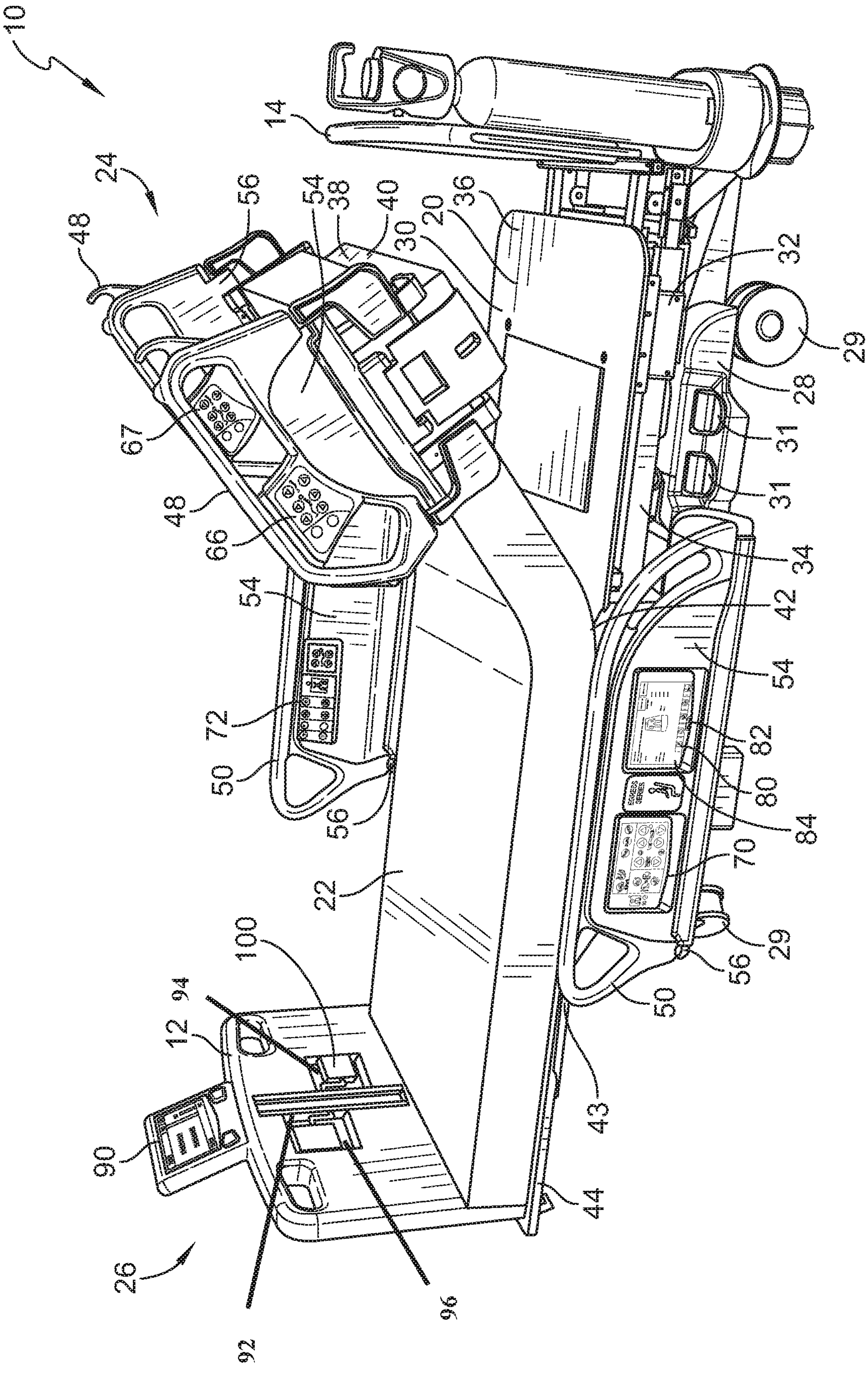
FIG. 1 is a side perspective view of a patient support apparatus in accordance with an embodiment and embodied as a hospital bed having a frame with a headboard, footboard, and side rails coupled to the frame.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Referring to FIG. 1, a patient support apparatus, such as illustrative hospital bed 10, includes a bed frame 20 that supports a surface or mattress 22 as shown in FIG. 1. Notably, the present disclosure is applicable to other patient support apparatuses including, for example, other types of beds, patient tables, stretchers, wheel chairs, and the like. Furthermore, use of the term "hospital bed" herein is intended to mean beds that support patients in all types of settings including, for example, nursing homes, outpatient facilities, medical clinics, and even a patient's own home, and is not intended to imply that such beds must be located in a hospital. As will be described in further detail below, the present disclosure is focused primarily on various exercise apparatuses that may be incorporated into bed 10.

Frame 20 of bed 10 includes a base frame 28, an upper frame assembly 30 and a lift system 32 coupling upper frame assembly 30 to base frame 28. Lift system 32 is operable to raise, lower, and tilt upper frame assembly 30 relative to base frame 28. Bed 10 has a head end 24 and a foot end 26 that is spaced from head end 24 in a longitudinal dimension of bed 10. Hospital bed 10 further includes a footboard 12 at the foot end 26 and a headboard 14 at the head end 24. Base frame 28 includes wheels or casters 29 that roll along a floor (not shown) as bed 10 is moved from one location to another. A set of foot pedals 31 are coupled to base frame 28 and are used to brake and release casters 29.

Illustrative hospital bed 10 has four side rail assemblies coupled to upper frame assembly 30 as shown in FIG. 1. The four side rail assemblies include a pair of head side rail assemblies 48 (sometimes referred to as head rails) and a pair of foot side rail assemblies 50 (sometimes referred to as foot rails). Side rails 48 are spaced from each other in a lateral dimension of bed 10 and the same can be said of side rails 50. Each of the side rail assemblies 48, 50 is movable between a raised position, as shown in FIG. 1, and a lowered position (shown in FIG. 1 for the foot rail 50 on the left side of the bed 10). Side rail assemblies 48, 50 are sometimes referred to herein as side rails 48, 50. Each side rail 48, 50 includes a barrier panel 54 and a linkage 56. Each linkage 56 is coupled to the upper frame assembly 30 and is configured to guide the barrier panel 54 during movement of side rails 48, 50 between the respective raised and lowered positions. Barrier panel 54 is maintained by the linkage 56 in a substantially vertical orientation during movement of side rails 48, 50 between the respective raised and lowered positions.

Upper frame assembly 30 includes a lift frame 34, a weigh frame 36 supported with respect to lift frame 34, and a patient support deck 38 carried by weigh frame 36. Each of frames 34, 36, 38, either individually of collectively, is considered to be an "upper frame" according to this disclosure. Thus, patient support apparatuses that omit one or more of frames 34, 36, 38 but yet still have an upper frame are within the scope of this disclosure. So, basically, the upper frame is considered to be the portion of bed frame 20 that is moved by lift system 32 relative to base frame 30, regardless of its configuration. Accordingly, upper frame assembly 30 is sometimes referred to herein as simply upper frame 30.

Patient support deck 38 is carried by weigh frame 36 and engages a bottom surface of mattress 22. Patient support deck 38 includes a head section 40, a seat section 42, a thigh section 43 and a foot section 44 in the illustrative example as shown in FIG. 1. The placement of reference numerals 40, 42, 43, 44 in FIG. 1 generally denotes the location of the corresponding sections. Sections 40, 43, 44 are each movable relative to weigh frame 36. For example, head section 40 pivotably raises and lowers relative to seat section 42 whereas foot section 44 pivotably raises and lowers relative to thigh section 43. Additionally, thigh section 43 articulates relative to seat section 42. Also, in some embodiments, foot section 44 is extendable and retractable to change the overall length of foot section 44 and therefore, to change the overall length of deck 38.

In the illustrative embodiment, seat section 42 is fixed in position with respect to weigh frame 36 as patient support deck 38 moves between its various patient supporting positions including a horizontal position, shown in FIG. 1, to support the patient in a supine position, for example, and a chair position (not shown) to support the patient in a sitting up position. In other embodiments, seat section 42 also moves relative to weigh frame 36, such as by pivoting and/or translating. Of course, in those embodiments in which seat section 42 translates along upper frame 42, the thigh and foot sections 43, 44 also translate along with seat section 42.

Bed 10 includes one or more motors or actuators, which in some embodiments, comprise linear actuators with electric motors to move the various sections 40, 43, 44 relative to frame 36 and operate lift system 32 to raise, lower, and tilt upper frame assembly 30 relative to base frame 28. These actuators are well-known in the hospital bed art and thus, are not illustrated herein. Alternative actuators or motors contemplated by this disclosure include hydraulic cylinders and pneumatic cylinders, for example.

Each side rail 48 includes a first user control panel 66 coupled to the outward side of the associated barrier panel 54 and each side rail 48 includes a second user control panel 67 coupled to the inward side of the associated barrier panel 54. Control panel 66 includes various buttons that are used by a caregiver (not shown) to control associated functions of bed 10 and control panel 67 includes various buttons that are used by a patient (shown in FIGS. 2 and 3, for example) to control associated functions of bed 10. For example, control panel 66 includes buttons that are used to raise and lower the head section 40, buttons that are used to operate knee motor to raise and lower the thigh section 43, and buttons that are used to raise, lower, and tilt upper frame assembly 30 relative to base frame 28. In the illustrative embodiment, control panel 67 includes buttons that are used to raise and lower the head, thigh, and foot sections 40, 43, 44. In some embodiments, the buttons of control panels 66, 67 comprise membrane switches. Additionally, each side rail 50 includes a first user control panel 70 coupled to the outward side of the associated barrier panel 54 and each side rail 50 includes a second user control panel 72 coupled to the inward side of the associated barrier panel 54.

The control panel 70 includes a graphical user interface 80 that includes a display 82 having inputs 84. The display 82 illustrates screens for an exercise regimen that may include exercises for the patient's quads, arms, or core. That is, a caregiver may utilize the display 82 to set the patient's exercise regimen. The exercise regimen may be set on a timer to alert the patient to exercise at a particular time, for example every four hours. In some embodiments, the exercise regimen includes setting a time for performing a particular exercise, e.g. exercise quads for 5 minutes. The exercise regimen may also include setting a number of sets and a number of repetitions in each set. Also, the caregiver may set a resistance for each exercise. In some embodiments, a display 82 is also provided on the control panel 67 to enable the patient to set an exercise regimen.

The display 82 may also include information related to a bed position. For example, the display 82 may illustrate the bed 10 with references to the angles of each bed section, such as head section at 30 degrees. The display 82 may also display information related to a pressure of pressurized bladders in the mattress 22. In an embodiment where the bed 10 includes a weigh scale, the display 82 may display a weight of the patient. In an embodiment of the bed 10 that includes devices for detecting vital signs, the display 82 may include information related to the patient's vital signs. For example, the display 82 may illustrate information related to patient temperature, blood pressure, heart rate, etc.

Still referring to FIG. 1, a display 90 is attached to the footboard 12. The display 90 may be configured to display the same information as the display 82. The display 90 is positioned to be visible by the patient while performing exercises. The display 90 is also utilized to track the patient's progress. For example, the display 90 may track a number of repetitions in a set, e.g. 4 of 10 repetitions. In some embodiments, the display 90 is configured to provide encouraging statements to the patient. For example, the display 90 may display statements such as "good work," "3 reps to go," etc.

Foot pedals 100 are positioned in a recess 92 of the footboard 12 to enable the patient to exercise their quads. The foot pedals 100 move between a stowed positioned (shown in FIG. 1) and a deployed position (shown in FIGS. 2 and 3). In the stowed positioned, a right foot pedal 110 is stowed in a right foot pedal receiving portion 94 of the recess 92 and a left foot pedal 112 is stowed in a left foot pedal receiving portion 96 of the recess 92 so as to not interfere with the patient's legs and feet. When the patient is ready to exercise, the foot pedals 100 are moved out of the recess 92 to the deployed position.

Figure 2:
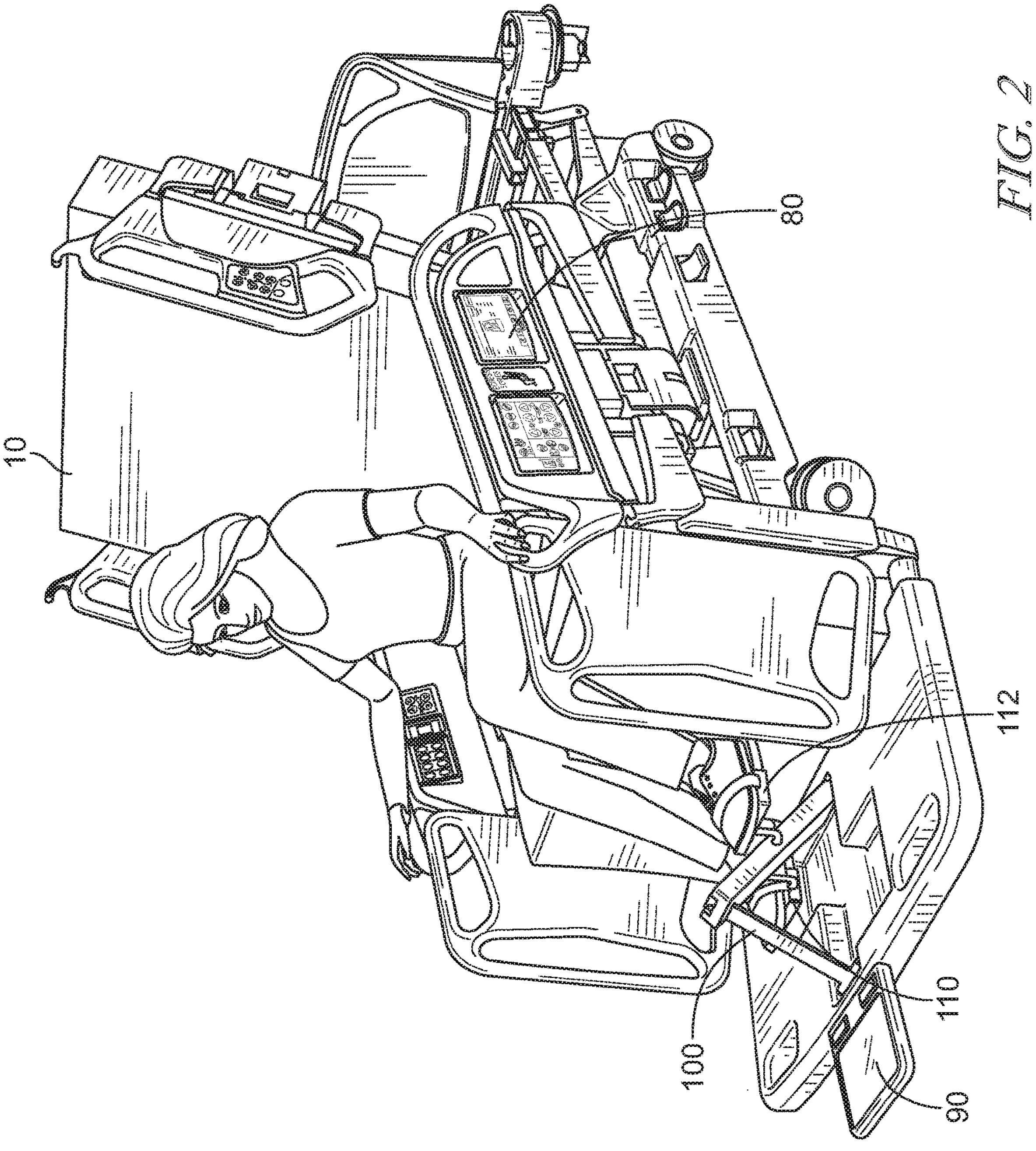
FIG. 2 is a side perspective view of the patient support apparatus shown in FIG. 1 and having a pair of arm levers attached to the frame, wherein the arm levers are illustrated in an extended position.
Figure 3:
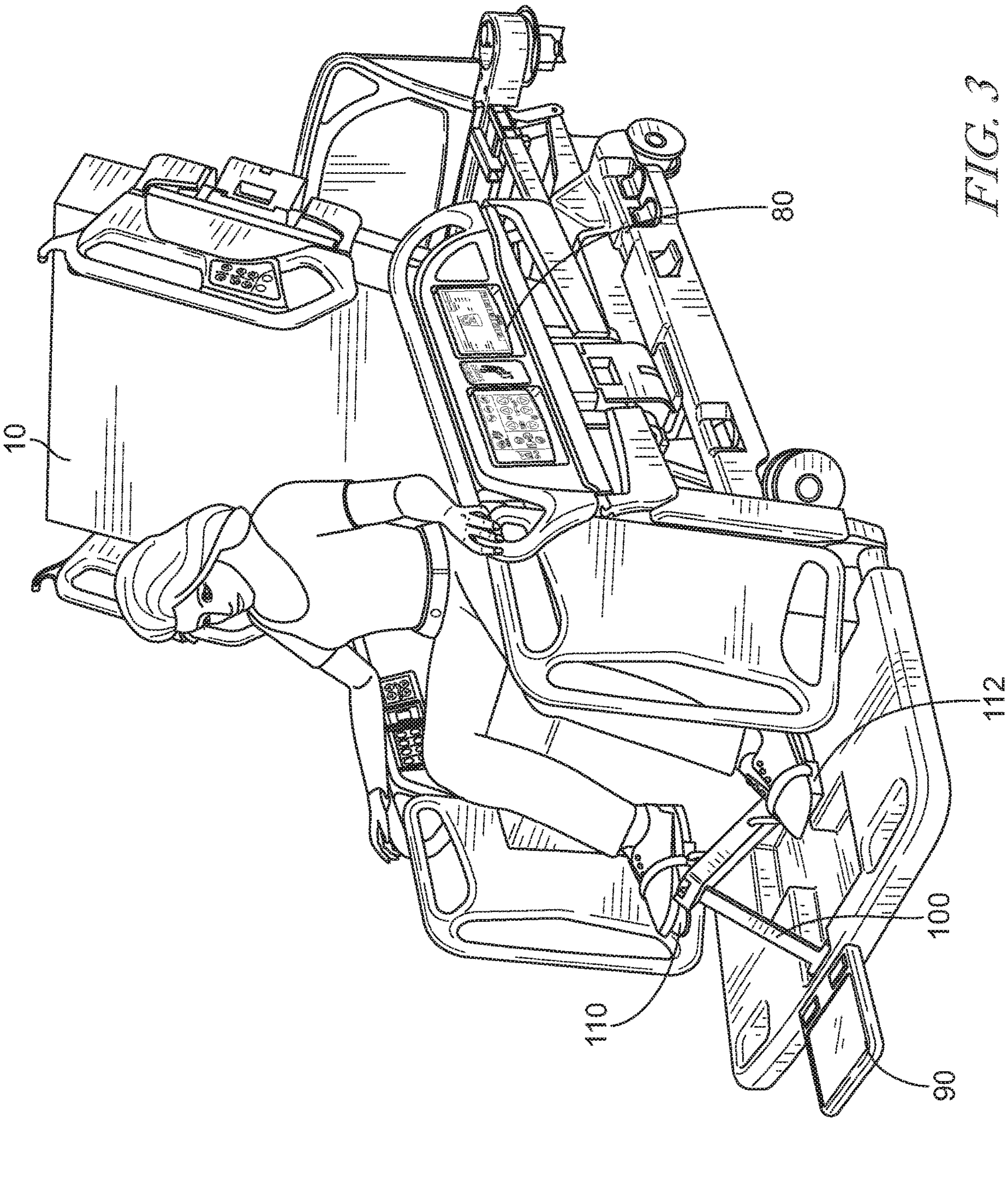
FIG. 3 is a side perspective view of the patient support apparatus shown in FIG. 1 and having a pair of arm levers attached to the frame, wherein the arm levers are illustrated in a retracted position.
Figure 4:
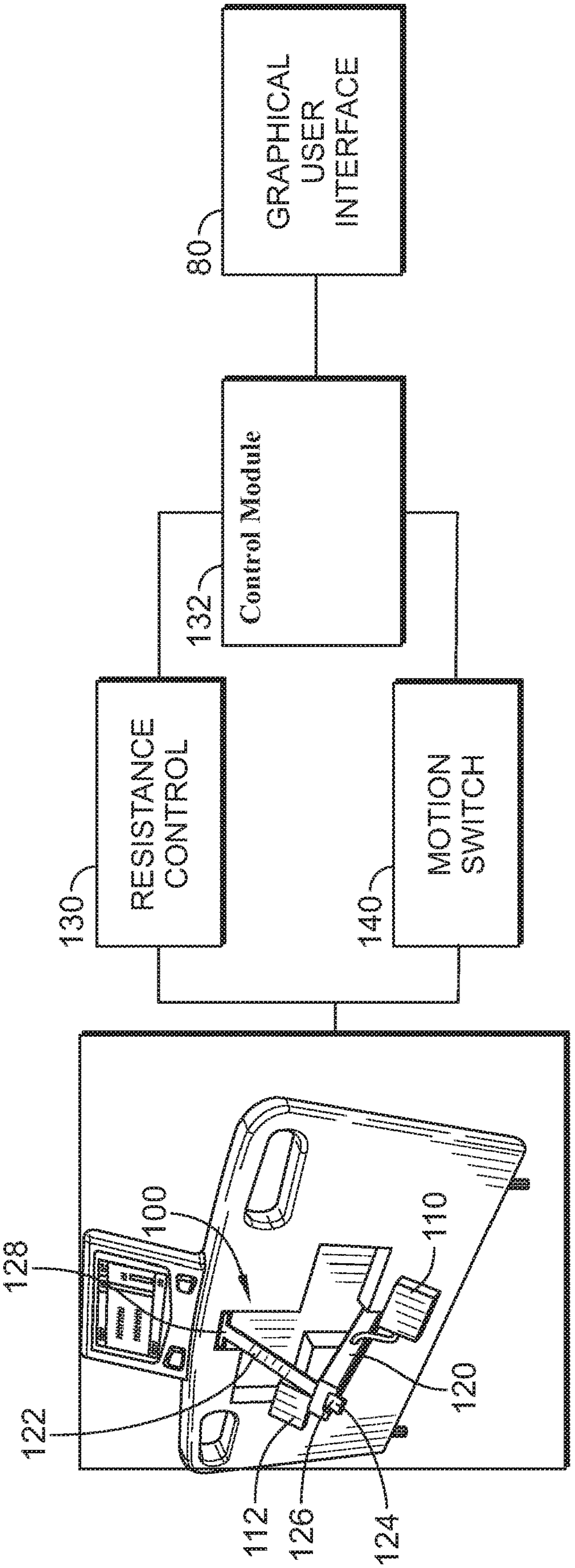
FIG. 4 is a schematic diagram of an arm lever in electronic communication with various electrical components that control the operation and monitoring of the arm lever.

Referring to FIGS. 2 and 3, the bed 10 is moved to a sitting position and the foot pedals 100 are moved to the deployed position to permit the patient to exercise the patient's quads and other leg muscles. As shown in FIG. 4, the foot pedals 100 includes a right pedal 110 for the patient's right foot and a left pedal 112 for the patient's left foot. The pedals 110, 112 are joined by a crank arm 114. The crank arm 114 is configured so that the pedals are offset. The pedals 110, 112 are configured to be rotated like bicycle pedals. The crank arm 114 extends through a first arm 120 that is rotatably connected at one end to the footboard 12. A second arm 122 has a first end 124 that movably extends through an opening 126 in the first arm 120 and a second end 128 that is rotatably secured to the footboard 12. The second arm 122 slides through the first arm 120 as the second arm 122 and the first arm 120 rotate relative to the footboard 12 to move the pedals between the stowed position and the open position. FIG. 2 illustrates the pedals 110, 112 in a first position and FIG. 3 illustrates the pedals 110, 112 in a second position. As will be appreciated, the pedals 110, 112 can rotate repeatedly through as many revolutions as the patient can rotate them during an exercise session.

The caregiver may notify the patient that it is time to exercise. Optionally, a timer may be set at the bed 10 or a remote computer and an alert may notify the patient that it is time to exercise. In some embodiments, the patient may begin the quad exercises without any set exercise regimen. In other embodiments, the patient's exercise regimen is entered at the bed 10 or a remote computer prior to starting the workout. The caregiver and/or patient enters a goal time, e.g. 5 minutes, into the interface 80. Other information may also be set in the exercise regimen, for example a goal heartrate or a resistance of the pedals 100. As described in more detail below, in some embodiments, the resistance of the pedals 100 may be altered to fit the patient's exercise needs.

During the exercise, the patient's exercise time and number of revolutions is tracked. A total mileage pedaled, calories burned, and speed may also be determined and displayed on the display 90. The display 90 also shows a total time exercising and a remaining time in the exercise, in some embodiments. Throughout the exercise, the display 90 displays reminders and encouragement to the patient to finish the exercise. After the set time, the display 90 notifies the patient that the exercise is complete. As described in more detail below, data related to the patient's exercise is stored for future review.

Referring to FIG. 4, the pedals 100 are coupled to a resistance control 130 that controls a resistance of the pedals 100. The resistance control 130 may include a motor that applies a negative force to the pedals 100 to slow the patient's movement of the pedals 100. Alternatively, the resistance control 130 may include a wheel and brake pad that may be adjusted to adjust a level of resistance. A belt that applies adjustable resistance to a drum, or even directly to a central portion of crank arm 114, inside arm 120, is another example of a contemplated resistance control 130. The resistance control 130 may be electrically coupled to a control module 132, which is coupled to the interface 80. Accordingly, the caregiver my input a desired resistance into the interface 80. The interface 80 transmits a signal to the control module 132, which then adjusts the resistance control 130. The control module 132 is included as part of a bed controller or bed control circuitry of bed 10, in some embodiments. The control module 132 includes at least one processor, a memory, input/output ports, a clock, and any other necessary components to operate control circuitry. In another embodiment, the resistance control 130 may include a resistance band that is manually coupled to the pedals 100. The resistance band may be selected from a plurality of resistance bands, each providing a different resistance.

The pedals 100 are also coupled to a motion switch 140 that tracks the motion of the pedals 100. The motion switch 140 determines how many revolutions of the pedals 100 have been completed. The motion switch 140 may also determine a speed of the pedals 100. Data collected by the motion switch 140 is transmitted to the control module 132. The data includes information related to the speed and revolutions of the pedals. The control module 132 transmits the data to the interface 80 to display the data on the display 82. The data may also be displayed on the display 90.

Figure 5:
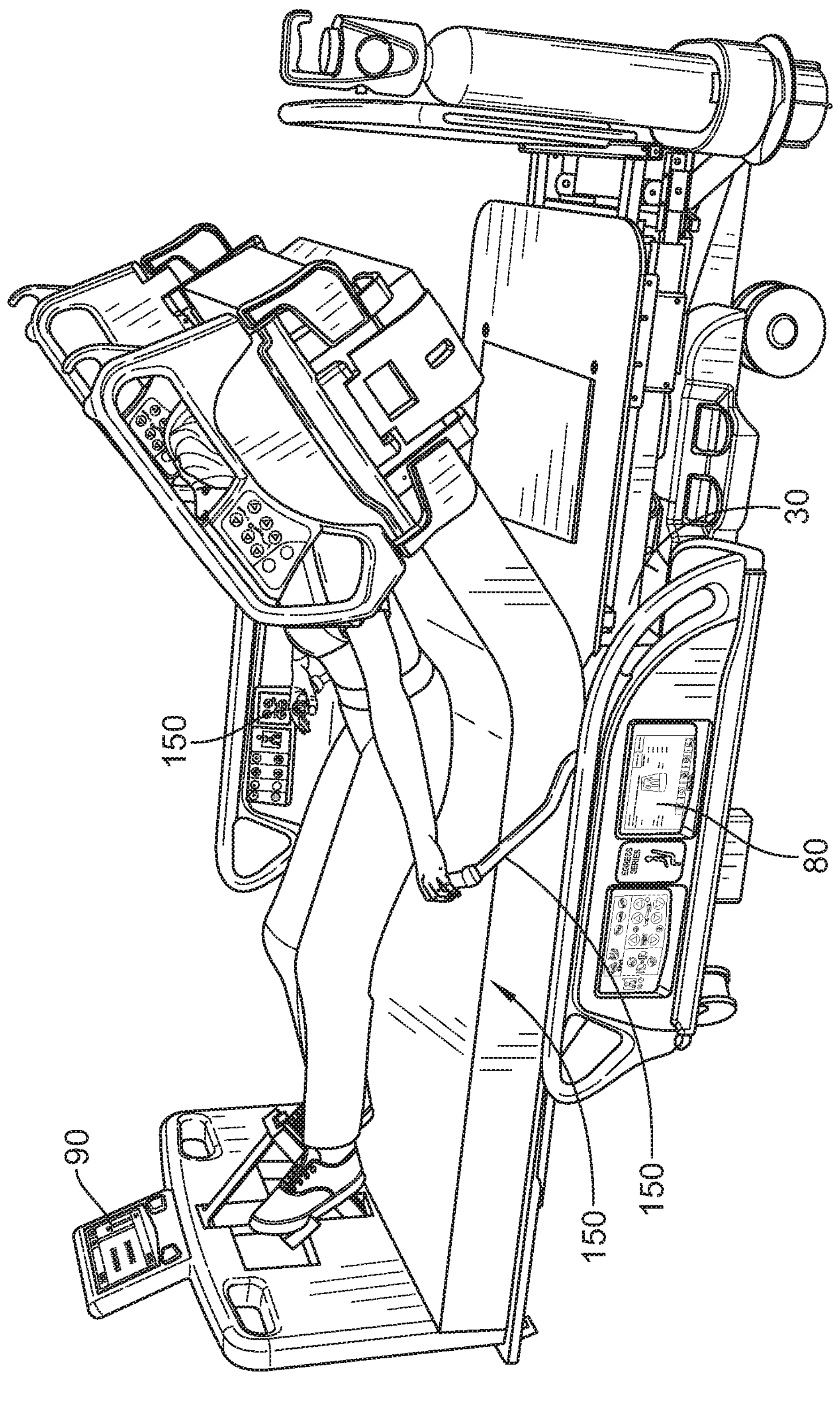
FIG. 5 is a foot end perspective view of the patient support apparatus shown in FIG. 1 having foot pedals in a first rotational position.
Figure 6:
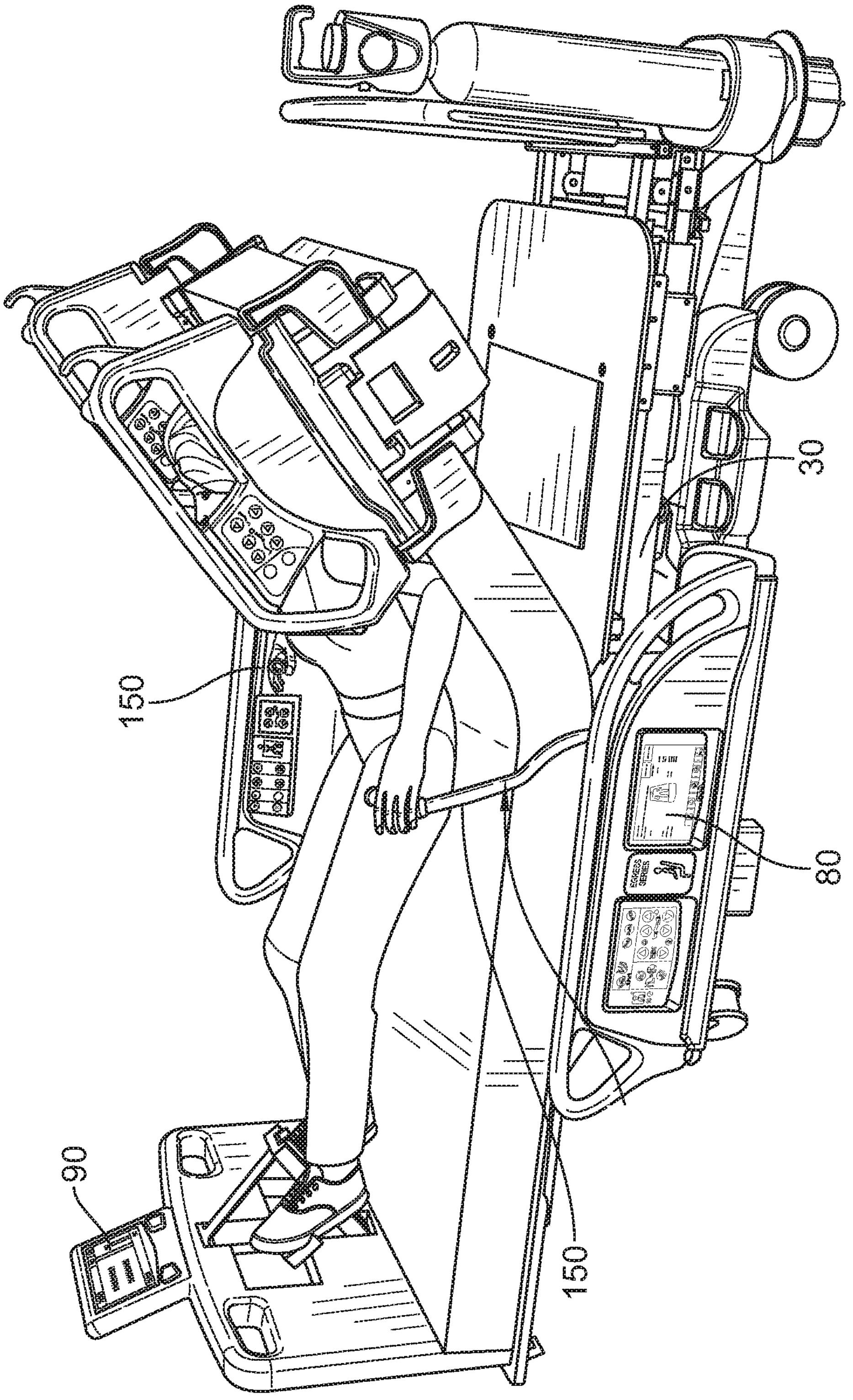
FIG. 6 is a foot end perspective view of the patient support apparatus shown in FIG. 1 having foot pedals in a second rotational position.
Figure 7:
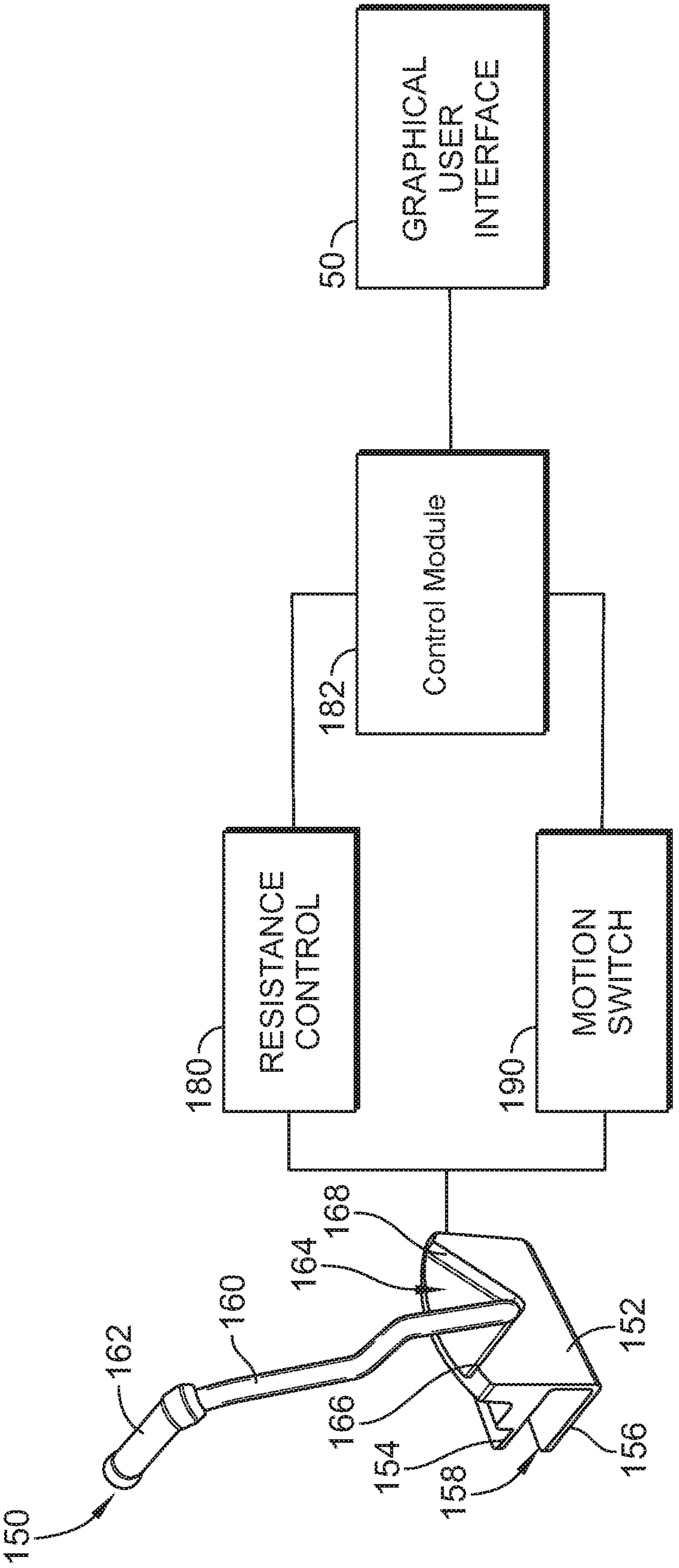
FIG. 7 is a schematic diagram of the foot pedals in electronic communication with various electrical components that control the operation and monitoring of the arm lever.

Referring now to FIGS. 5 and 6, arm levers 150 are coupled to the upper frame 30 to permit the patient to perform rowing exercises. A full arm lever assembly 150 is shown in FIG. 7. The arm lever assembly 150 includes a housing 152 having an upper flange 154 and a lower flange 156. A slot 158 is defined between the upper flange 154 and the lower flange 156. A portion of the upper frame 30 is positioned in the slot 158 so that the portion of the upper frame 30 is positioned between the upper flange 154 and the lower flange 156. The upper flange 154 and the lower flange 156 frictionally secure to the upper frame 30 to secure the arm lever assembly 150 to the upper frame 30, in some embodiments. In other embodiments, a threaded knob, a thumb screw, or the like extends through one of the flanges 154, 156 and is rotated to clamp and release arm lever assembly 150 to the respective portion of the upper frame 30. Multiple such knobs or thumb screws are used in some embodiments of arm lever assembly 150.

A lever 160 having a handle 162 extends from the housing 152. The patient grips the handle 162 during a rowing exercise. The lever 160 is configured to move within a pie-shaped recess 164 formed in the housing 152. The recess 164 extends from a first stop surface 166 to a second stop surface 168. The lever 160 is rotatably coupled to the housing 152 so that the lever 160 is movable between the first stop surface 166 to the second stop surface 168. As the lever 160 moves between the surfaces 166, 168, the lever 160 moves between an extended position (shown in FIG. 5) to a retracted position (shown in FIG. 6). In the extended position, lever 160 abuts surface 166, and in the retracted position, lever 160 abuts surface 168. Lever 160 moves through an arc of about 90 degrees when moving between the extended and retracted positions, as defined by abutment with surfaces 166, 168, respectively. In other embodiments, recess 164 is configured to permit movement of lever 160 through an arc greater than or less than 90 degrees.

Referring now to FIGS. 5 and 6, the caregiver may notify the patient that it is time to exercise. Optionally, a timer may be set at the bed 10 or at a remote computer and an alert may notify the patient that it is time to exercise. In some embodiments, the patient may begin the rowing exercises without any set exercise regimen. In other embodiments, the patient's exercise regimen is entered at the bed 10 or a remote computer prior to starting the workout. The caregiver and/or patient enters a goal, e.g. 3 sets and 10 repetitions per set, into the interface 80. Other information may also be set in the exercise regimen, for example a goal heartrate or a resistance of the levers 160. As described in more detail below, in some embodiments, the resistance of the levers 160 may be altered to fit the patient's exercise needs.

During the exercise, the patient's repetitions and sets are tracked. Calories burned and speed may also be determined and displayed on the display 90. The display 90 also shows a remaining sets and repetitions in the exercise. Throughout the exercise, the display 90 shows reminders and encouragement to the patient to finish the exercise. After the set time, the display 90 notifies the patient that the exercise is complete. As described in more detail below, data related to the patient's exercise is stored for future review.

Referring to FIG. 7, the levers 170 are coupled to a resistance control 180 that controls a resistance of the levers 170. The resistance control 180 may be a motor that applies a negative force to the levers 170 to slow the patient's movement of the levers 170. Alternatively, the resistance control 180 may include a wheel and brake pad that may be adjusted to adjust a level of resistance. The resistance control 180 may be electrically coupled to a control module 182, which is coupled to the interface 80. In some embodiments, the control module 182 is positioned within the housing 152. The housing 152 may include an electrical connection (not shown) to electrically connect the control module 182 to the bed 10 and the interface 80. In other embodiments, the control module 182 wirelessly communicates with control circuitry of the bed 10 to display information on and to communicate with the interface 80. Control module 182 is included as part of a bed controller or bed control circuitry of bed 10, in some embodiments. In some embodiments, the control module 182 is the same module as the control module 132. The control module 182 includes at least one processor, a memory, input/output ports, a clock, and any other necessary components to operate control circuitry. Accordingly, the caregiver my input a desired resistance into the interface 80. The interface 80 transmits a signal to the control module 182, which then adjusts the resistance control 180. In another embodiment, the resistance control 180 may be a resistance band that is manually coupled to the levers 160. The resistance band may be selected from a plurality of resistance bands, each providing a different resistance.

The levers 160 are also coupled to a motion switch 190 that tracks the motion of the levers 160. The motion switch 190 determines how many times the lever 160 is moved between the first stop surface 166 and the second stop surface 168. If the patient does not entirely move the lever 160 to one of the first stop surface 166 or the second stop surface 168, the display 82 or the display 90 may notify the patient that the repetition was not fully completed. Alternatively, motion by the lever 160 through a substantial portion of the arc, such as two-thirds or 80%, is counted as a completed repetition, in some embodiments. The motion switch 190 may also determine a speed of the levers 160. Data collected by the motion switch 190 is transmitted to the control module 182. The data includes information related to the number of repetitions, number of sets, and speed. The control module 182 transmits the data to the interface 80 to display the data on the display 82. The data may also be displayed on the display 90.

Figure 8:
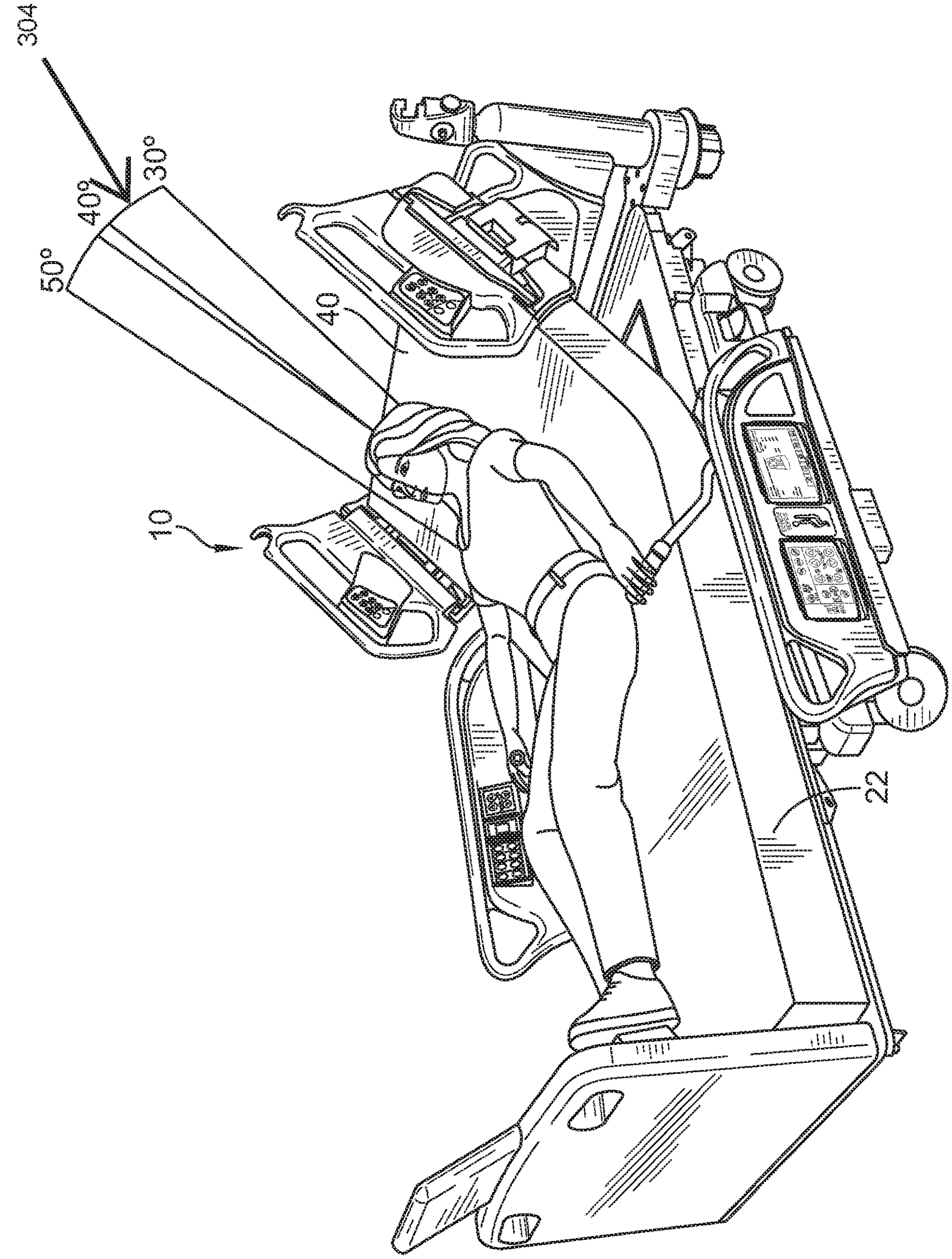
FIG. 8 is a side perspective view of the patient support apparatus shown in FIG. 1 and having a head section that raises and lowers to assist a patient in performing sit ups.

As illustrated in FIG. 8, the head section 40 is configured to assist the patient in performing sit ups. In such an embodiment, one or more strain gauges 200 (FIG. 9) may be positioned in or on one of the mattress 22 or the head section 40. Each strain gauge 200 is configured to monitor a force or pressure applied by the weight of the patient. As the patient raises their upper body in a sit up, the strain gauge 200 detects a reduction in force or pressure. When a predetermined reduction in force or pressure in detected, the head section 40 is raised to assist the patient in performing the sit up. In the illustrative embodiment, the head section 40 raises between 30 degrees and 50 degrees to assist the patient. It should be noted that other ranges of head section movement are contemplated to assist the patient. For example, the range may be any range between 0 degrees and 90 degrees. A resistance of the patient's exercise may be altered by altering the predetermined reduction in force or pressure. For example, the head section 40 may begin assistance at the detection of any reduction in force or pressure. In other embodiments, the predetermined reduction in force or pressure may be set by the caregiver or patient, e.g. 10% reduction in force or pressure, 15% reduction in force or pressure, 20% reduction in force or pressure, etc. The predetermine reduction in pressure may be based on a weight of the patient, for example. In other embodiments, one or more force sensitive resistors (FSR's) or other types of sensors are provided in mattress 22 or on the head section 40 in addition to, or in lieu of, one or more strain gauges.

Figure 9:
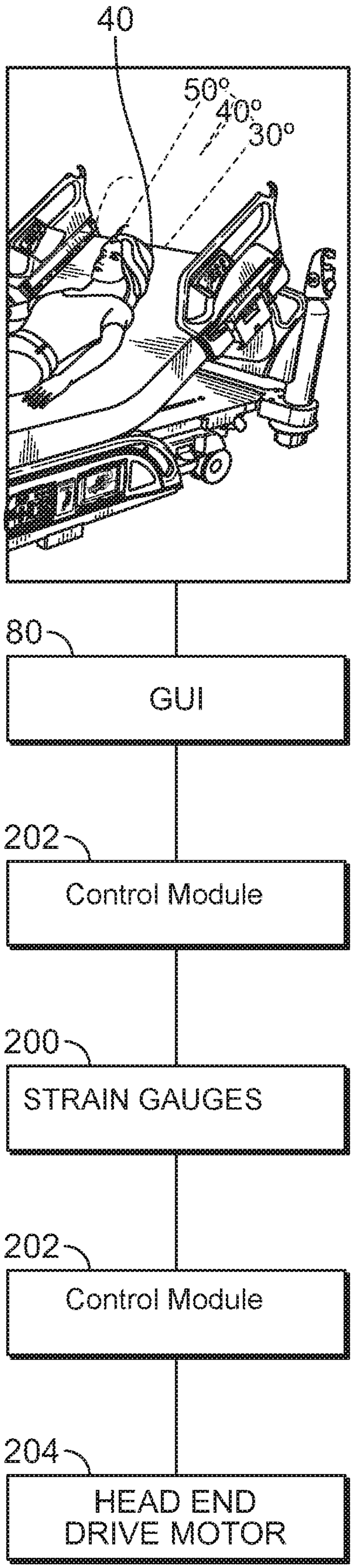
FIG. 9 is a schematic diagram of the head section in electronic communication with various electrical components that control the operation and monitoring of the arm lever.

Referring to FIG. 9, the patient's exercise regimen is entered into the interface 80. The regimen may include a number of sets and a number of repetitions per set. The regimen may also include the predetermined reduction in force or pressure, e.g. resistance. The exercise regimen is communicated to a control module 202, which monitors the strain gauge 200. Control module 202 is included as part of a bed controller or bed control circuitry of bed 10, in some embodiments. In some embodiments, the control module 202 is the same module as the control module 132 and/or control module 182. The control module 202 includes at least one processor, a memory, input/output ports, a clock, and any other necessary components to operate control circuitry. The strain gauge 200 communicates the reduction in force or pressure to the control module 202. When the predetermined reduction in force or pressure is reached, the control module 202 communicates with a head end motor 204 to control movement of the head end motor 204. Control of the head end motor 204 may operate continuously. For example, the head end motor 204 may be operated as long as the predetermined reduction in force or pressure is reached. If the patient begins to rest back on the head section 40 so that the predetermined reduction in force or pressure is no longer achieved, the head end motor 204 may be slowed or stopped to slow or stop the movement of the head section 40. Data related to the patient's core exercise may displayed on the displays 82 and/or 90. Additionally, as set forth above, the display 90 may communicate with the patient throughout the exercise to encourage the patient and notify the patient of progress.

Figure 10:
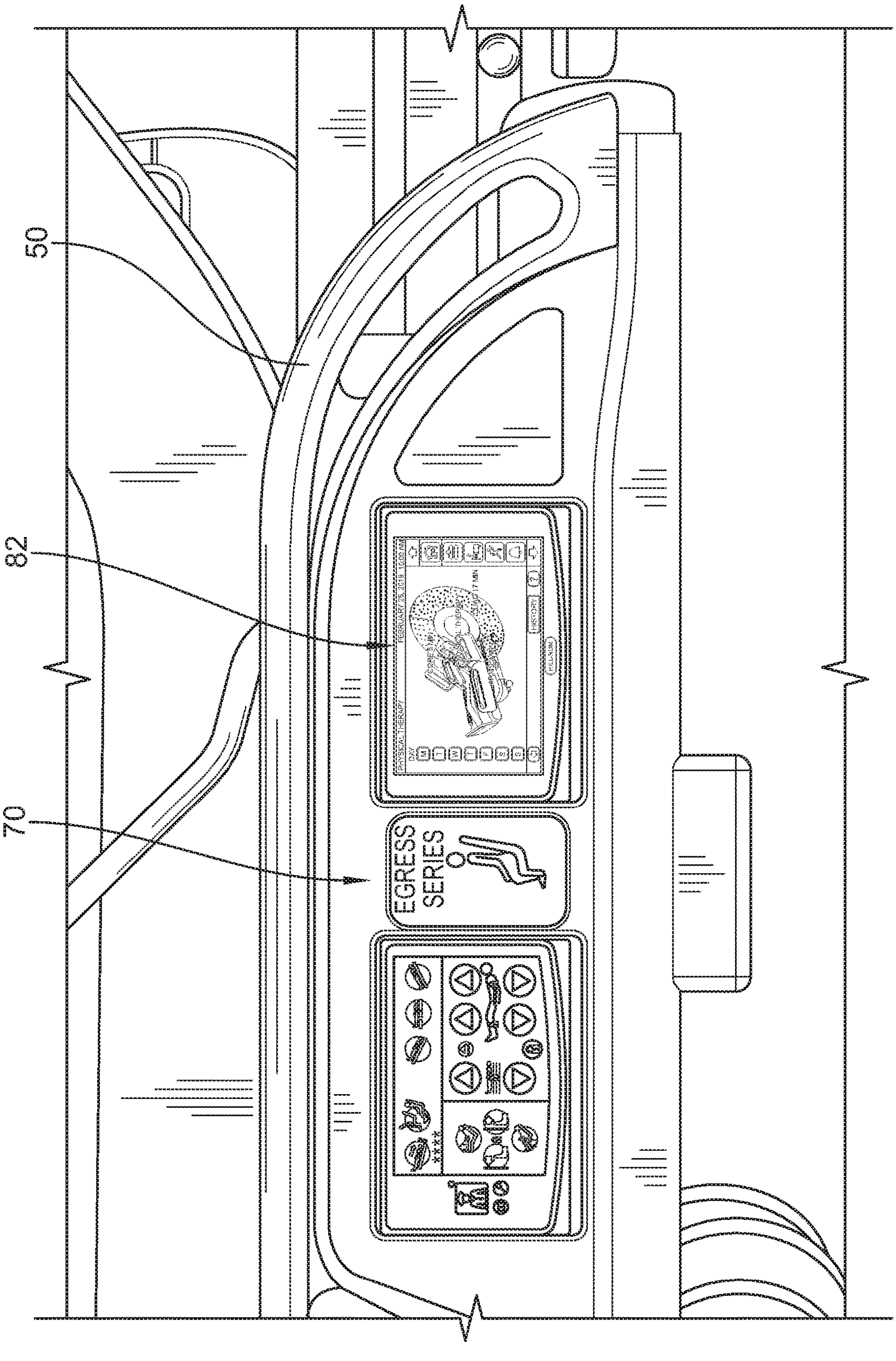
FIG. 10 is a side elevation view of a graphical user interface positioned on a side rail of the patient support apparatus shown in FIG. 1.

As illustrated in FIG. 10, the display 82 is provided on the control panel 70. The display 82 shows screens related to the patient's exercise regimen. The interface 80 provides a location for the patient and/or caregiver to enter data related to the exercise regimen, for example number of sets, number of repetitions per set, and a resistance. The display 82 also shows information and data tracking the patient's progress. In some embodiments, the display 82 may show a number of repetitions that the patient has performed. The display 82 may also show a history of the patient's exercise regimens.

Figure 11:
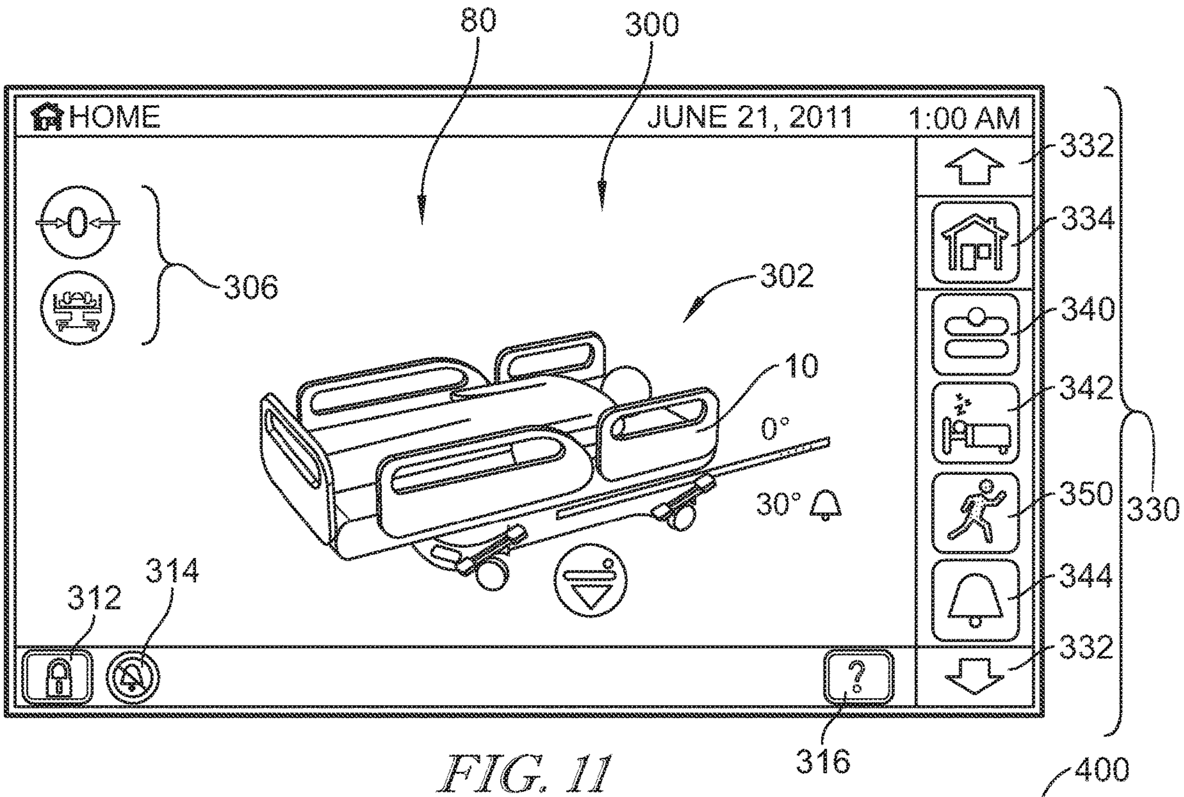
FIG. 11 is a view of a home screen display that is displayed on the graphical user interface.

A home screen 300 of the display 82 is illustrated in FIG. 11. The home screen 300 shows a current position 302 of the patient in the bed 10 and indicates a head angle 304 of the bed 10. The angle and position of the bed 10 is also illustrated in icons 306 in the upper left corner of the screen 300. In the lower left corner 310 of the screen 300, a "lock" icon 312 enables a user to lock the home screen 300 and prevent the entry of exercises into the interface 80. An "alarm" icon 314 may also be set to activate an alarm if the bed setting are tampered with. In the illustrative embodiment, the "alarm" icon 314 is turned off. A "help" icon 316 provides troubleshooting instructions for the operator.

A list of main function icons 330 is provided in the right side of the display 82. The main function icons 330 enable the patient and/or caregiver to set various functions of the bed 10. Scrolling icons 332 enable the user to scroll through the main function icons 330. A "home" icon 334 can be selected at any time to return the user to the home screen 300. A "bed adjust" icon 340 may be selected to populate a screen that enables the user to alter a position of the bed 10, e.g. raise the head section of the bed 10, lower the foot section of the bed 10, etc. A "sleep" icon 342 may be selected to indicate that the patient is asleep. The "sleep" icon 342 may temporarily suspend certain functions of the bed 10. For example, is the bed 10 is programmed to alert the patient every 2 hours to exercise, such an alert may be suspended while the "sleep" icon 342 is activated. An "alarm" icon 344 may activate an alarm. An "exercise" icon 350 populates various screens related to the patient's exercise regimen. For example, the "exercise" icon 350 may populate a physical therapy history screen 400, as illustrated in FIG. 12.

Figure 12:
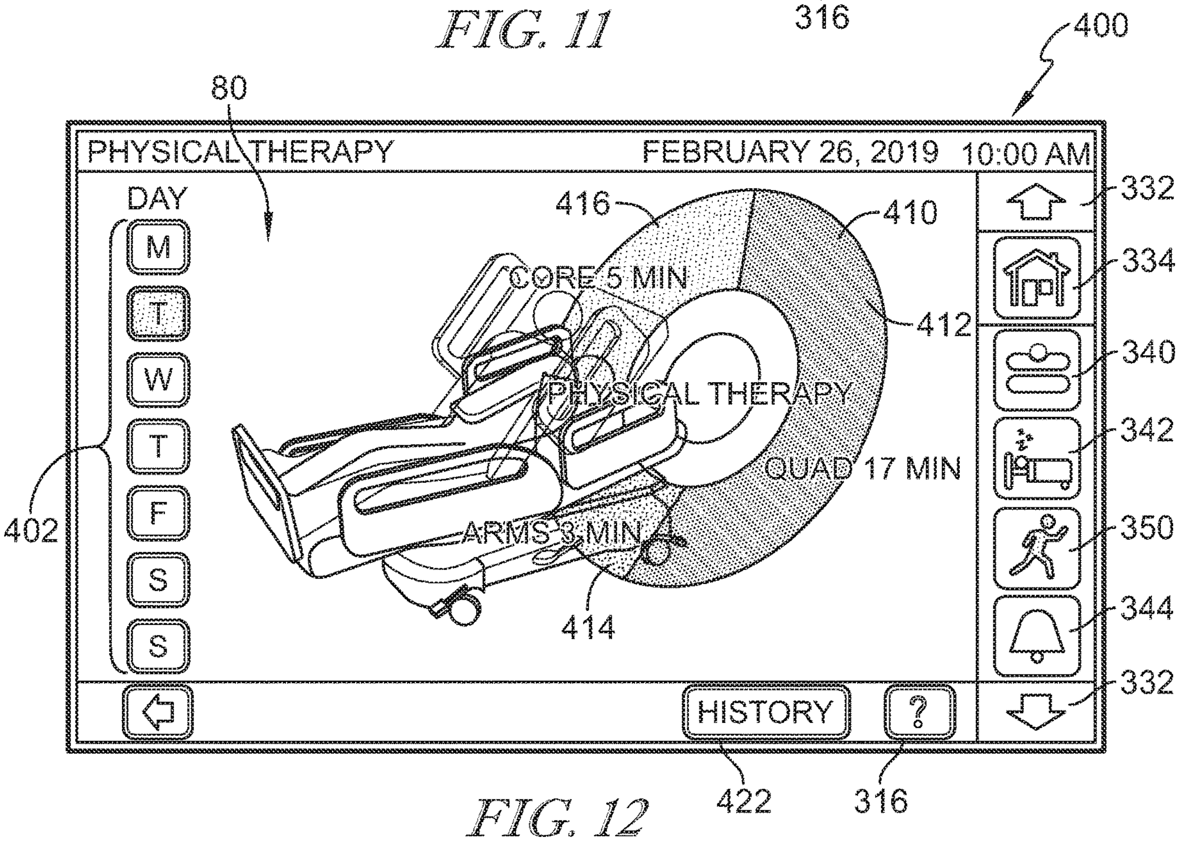
FIG. 12 is a view of a physical therapy display that is displayed on the graphical user interface.

Referring now to FIG. 12, the physical therapy history screen 400 includes day icons 402 for entering various exercise regimen parameters. The day icons 402 include a Monday, Tuesday, Wednesday, Thursday, Friday, Saturday, and Sunday icon to select the respective day of the week. The screen 400 includes a graph 410 that breaks down the patient's exercise for the selected day. In the illustrative embodiment, the graph 410 highlights the patient's exercise for Tuesday. The graph 410 includes a wedge 412 highlighting 17 minutes of quad exercises with the foot pedals 100, a wedge 414 highlights 3 minutes of arm exercise with the arm lever assembly 150, and a wedge 416 highlights 5 minutes of core exercises, for a total of 25 minutes of exercise. Such a graph 410 is provided for each day of the week as selected with the day icons 402. In some embodiments, the wedges 412, 414, and 416 may be selected to alter an exercise parameter.

Figure 13:
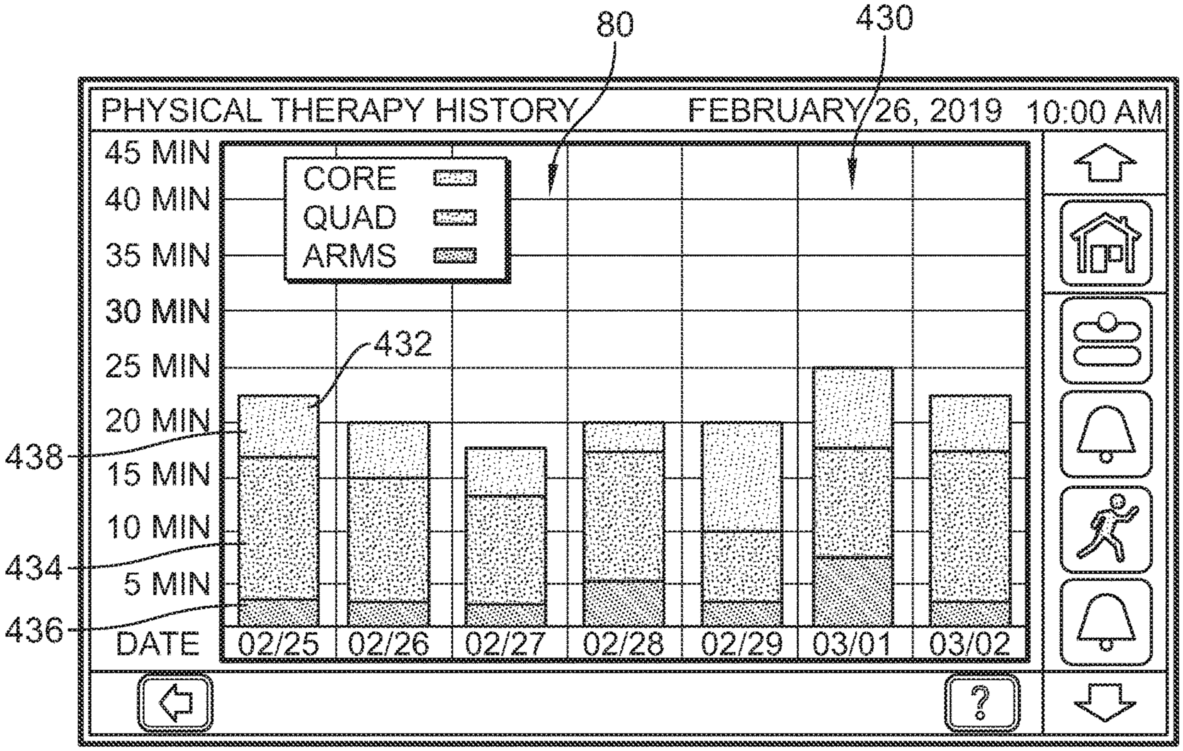
FIG. 13 is a view of a physical therapy history display that is displayed on the graphical user interface.

The physical therapy screen 400 includes all of the main function icons 330 and a "back" button 420. A "history" icon 422 may be selected to illustrate the entire week history of exercise for the patient. Referring to FIG. 13, a physical therapy history graph 430 illustrates a bar 432 indicating the total time exercised for each day of the week. Notably, the bar 432 is divided into smaller bars including a quad exercise bar 434, an arm exercise bar 436, and a core exercise bar 438. In the illustrative embodiment, the graph 430 illustrates the last seven days of exercise. In other embodiments, the user may select a different time frame, e.g. the previous week. In some embodiments, the therapy history is stored in an electronic medical record.

The bed 10 includes three therapeutic early mobility exercises. First, the normal footboard is replaced with a physical therapy footboard that incorporates a stowable bicycle type exercise apparatus 100. This footboard is connected to the control module to enable data tracking of the patients exercise. Second, a pair of "bolt on" rowing type exercise handles 150 allow for therapeutic exercise of the arms. The handles are also connected to the control module for data tracking. Finally, the head section utilizes the head section strain gauges or other suitable sensors to allow for a simulated therapeutic sit-up that benefits the core. Available through the graphical user interface 80, the head section can simulate a sit-up and then display the relevant sit-up data on a history screen. This allows the patient and the physical therapist to see how the patient is progressing.

The graphical user interface 80 is connected to the therapy accessories by means of electronic connections to the unit control block, actuators, motion switches and strain gauges. The controller or control circuitry of bed 10 is programmed to control these physical therapy devices, monitor and record performance data. This information is displayed to the caregiver via the graphical user interface 80 and also allows for interaction of physical therapy accessory settings. The display of the data consists of a discrete break down of the patient's performance with respect to the quads, arm, and core therapies. In addition the graphical user interface 80 allows for viewing of the data on a day-to-day, weekly, or monthly basis. Some embodiments also feature an intuitive "at a glance" novel layout of the presented info that could be more beneficial for users that don't necessarily like to view data solely on a bar graph.

The bed 10 offers early mobility exercise. In addition, by addressing additional muscle groups the patient's chances of benefiting from early mobility therapies are greatly increased. This translates to lower morbidity rates for patients confirmed by many early mobility studies. For care institutions, this concept translates to quicker recovery times for patients and all the revenue benefits that are associated. The bed 10 offers a safe and efficient solution to the hassles physical therapists face on a regular basis while trying to move highly acute patients to other devices or areas of the hospitals. Because the bed 10 offers mobility therapies incorporated into the patient platform, caregivers are more likely to use them. In addition, the availability of these exercises also allows the patient access to therapeutic exercises that can be done on their own. This could lead to a sense of empowerment allowing for better patient outcomes.

The advantages that arise from the software of the exercise devices are a unique way to track and display patient physical therapy data on a patient platform equipped with physical therapy capability. In addition, the ability of the software to capture, store and then send the data to the patient's electronic medical record allows for a better awareness of the patient's progress. Furthermore, capturing the data and sending it to the electronic medical record can reduce charting errors and allow for more accurate patient charting. This ability in turn can lead to earlier interventions if the patient's progress is flat or even negative. Finally, the ability to better monitor the patient's physical therapy state may lead to better patient outcomes.

Any theory, mechanism of operation, proof, or finding stated herein is meant to further enhance understanding of principles of the present disclosure and is not intended to make the present disclosure in any way dependent upon such theory, mechanism of operation, illustrative embodiment, proof, or finding. It should be understood that while the use of the word preferable, preferably or preferred in the description above indicates that the feature so described can be more desirable, it nonetheless cannot be necessary and embodiments lacking the same can be contemplated as within the scope of the disclosure, that scope being defined by the claims that follow.

In reading the claims it is intended that when words such as "a," "an," "at least one," "at least a portion" are used there is no intention to limit the claim to only one item unless specifically stated to the contrary in the claim. When the language "at least a portion" and/or "a portion" is used the item can include a portion and/or the entire item unless specifically stated to the contrary.

It should be understood that only selected embodiments have been shown and described and that all possible alternatives, modifications, aspects, combinations, principles, variations, and equivalents that come within the spirit of the disclosure as defined herein or by any of the following claims are desired to be protected. While embodiments of the disclosure have been illustrated and described in detail in the drawings and foregoing description, the same are to be considered as illustrative and not intended to be exhaustive or to limit the disclosure to the precise forms disclosed. Additional alternatives, modifications and variations can be apparent to those skilled in the art. Also, while multiple inventive aspects and principles can have been presented, they need not be utilized in combination, and many combinations of aspects and principles are possible in light of the various embodiments provided above.

The invention claimed is:

1. A patient support apparatus comprising:

a frame, a headboard and footboard coupled to the frame, a pair of side rails coupled to the frame, a control module positioned on the frame, a graphical user interface in communication with the control module, and an exercise apparatus coupled to the frame and in communication with the control module, wherein the control module is configured to control an operation of the exercise apparatus, and wherein the graphical user interface displays information related to the operation of the exercise apparatus, wherein the exercise apparatus includes a head section of the frame, wherein the head section raises and lowers as a user performs sit ups, wherein the head section includes a strain gauge to measure movement of the user relative to the head section, wherein movement of the user is measured by measuring a reduction in pressure on the head section with the strain gauge, wherein, when a predetermined reduction in pressure is detected, the head section is raised to assist the user in performing the sit up, and wherein a resistance of the sit up is altered by altering the predetermined reduction in pressure required for the head section to be raised to assist the user in performing the sit up.

2. The patient support apparatus of claim 1, wherein the graphical user interface includes user inputs that enable the user to input an exercise regimen into the control module, the control module controlling the exercise apparatus based on the exercise regimen.

3. The patient support apparatus of claim 2, wherein the control module tracks the user's progress of the exercise regimen.

4. The patient support apparatus of claim 3, wherein the graphical user interface displays data related to the user's progress of the exercise regimen.

5. The patient support apparatus of claim 2, wherein the exercise regimen includes at least one of a number of sets, a number of repetitions, and the resistance.

6. The patient support apparatus of claim 1, wherein the graphical user interface is positioned on the footboard.

7. The patient support apparatus of claim 1, further comprising a motion switch to track the motion of the exercise apparatus, the motion switch transmitting data related to the motion of the exercise apparatus to the control module.

8. The patient support apparatus of claim 1, wherein the exercise apparatus includes a resistance control to control the resistance of the exercise apparatus.

9. The patient support apparatus of claim 8, wherein the resistance control includes a motor.

10. The patient support apparatus of claim 8, wherein the resistance control includes a resistance band.

11. The patient support apparatus of claim 8, wherein the resistance control is controlled with user inputs on the graphical user interface.

12. The patient support apparatus of claim 1, wherein the exercise apparatus includes foot pedals coupled to the footboard.

13. The patient support apparatus of claim 12, wherein the frame includes a foot section that lowers to enable use of the foot pedals.

14. The patient support apparatus of claim 1, further comprising a motor to raise and lower the head section.

15. The patient support apparatus of claim 1, wherein the exercise apparatus includes a pair of arm levers, wherein each arm lever of the pair of arm levers is coupled to the frame.

16. The patient support apparatus of claim 1, wherein the predetermined reduction in pressure is configured to be set by at least one of a caregiver or the patient.

17. The patient support apparatus of claim 1, wherein the predetermined reduction in pressure is at least one of a 10% reduction in pressure, a 15% reduction in pressure, and a 20% reduction in pressure.

18. The patient support apparatus of claim 1, wherein the resistance of the sit up is further altered by altering a range of movement of the head section when the head section is raised to assist the user in performing the sit up.

* * * * *